(12) United States Patent
D'Ambrosio

(10) Patent No.: US 8,766,788 B2
(45) Date of Patent: Jul. 1, 2014

(54) TRANSCUTANEOUS ENERGY TRANSFER SYSTEM WITH VIBRATION INDUCING WARNING CIRCUITRY

(75) Inventor: Ralph L. D'Ambrosio, Wenham, MA (US)

(73) Assignee: Abiomed, Inc., Danvers, MA (US)

( * ) Notice: Subject to any disclaimer, the term of this patent is extended or adjusted under 35 U.S.C. 154(b) by 7 days.

(21) Appl. No.: 13/328,623

(22) Filed: Dec. 16, 2011

(65) Prior Publication Data

US 2012/0154143 A1 Jun. 21, 2012

Related U.S. Application Data

(60) Provisional application No. 61/425,164, filed on Dec. 20, 2010.

(51) Int. Cl.
*G08B 1/08* (2006.01)

(52) U.S. Cl.
USPC ............... 340/539.11; 340/7.6; 340/573.1

(58) Field of Classification Search
USPC .......... 340/539.11, 539.1, 539.12, 538.16, 340/539.24, 539.3, 463, 7.6, 7.32, 573.1
See application file for complete search history.

(56) References Cited

U.S. PATENT DOCUMENTS

| | | |
|---|---|---|
| 3,195,038 A | 7/1965 | Fry |
| 3,195,540 A | 7/1965 | Waller |
| 3,357,432 A | 12/1967 | Sparks |
| 3,357,434 A | 12/1967 | Abell |
| 3,711,747 A | 1/1973 | Sahara et al. |
| 3,756,246 A | 9/1973 | Thaler et al. |
| 3,824,129 A | 7/1974 | Fagan, Jr. |
| 3,825,925 A | 7/1974 | Drusch |
| 3,866,616 A | 2/1975 | Purdy et al. |
| 3,867,950 A | 2/1975 | Fischell |
| 3,888,260 A | 6/1975 | Fischell |
| 3,915,038 A | 10/1975 | Malin |
| 3,934,177 A | 1/1976 | Horbach |
| 3,942,535 A | 3/1976 | Schulman |
| 3,987,799 A | 10/1976 | Purdy et al. |
| 3,995,137 A | 11/1976 | Okada et al. |
| 4,011,499 A | 3/1977 | Betsill et al. |
| 4,012,769 A | 3/1977 | Edwards et al. |
| 4,041,955 A | 8/1977 | Kelly et al. |
| 4,068,292 A | 1/1978 | Berry et al. |

(Continued)

FOREIGN PATENT DOCUMENTS

| | | |
|---|---|---|
| DE | 2720011 A1 | 11/1978 |
| EP | 0 507 360 A2 | 10/1992 |

(Continued)

OTHER PUBLICATIONS

[No Author Listed] SBS 1.1—Compliant Gas Gauge and Protection Enabled with Impedance Track™, Texas Instruments, SLUS757B—Jul. 2007, Revised Apr. 2008. 18 pages.

(Continued)

*Primary Examiner* — Daniel Previl
(74) *Attorney, Agent, or Firm* — Thomas J. Engellenner; Reza Mollaaghababa; Pepper Hamilton LLP

(57) ABSTRACT

An improved alarm device for use in a transcutaneous energy transfer (TET) system is provided. The device includes a processor configured to monitor at least one function of an implanted cardiac assist device and to generate an internal vibratory alarm.

5 Claims, 6 Drawing Sheets

(56) References Cited

U.S. PATENT DOCUMENTS

| | | | |
|---|---|---|---|
| 4,071,032 | A | 1/1978 | Schulman |
| 4,104,701 | A | 8/1978 | Baranowski |
| 4,134,408 | A * | 1/1979 | Brownlee et al. ............ 607/33 |
| 4,143,661 | A | 3/1979 | LaForge et al. |
| 4,186,749 | A | 2/1980 | Fryer |
| 4,266,533 | A | 5/1981 | Ryaby et al. |
| 4,441,210 | A | 4/1984 | Hochmair et al. |
| 4,441,498 | A | 4/1984 | Nordling |
| 4,517,585 | A | 5/1985 | Ridout et al. |
| 4,539,433 | A | 9/1985 | Ishino et al. |
| 4,586,508 | A | 5/1986 | Batina et al. |
| 4,665,896 | A | 5/1987 | LaForge et al. |
| 4,673,888 | A | 6/1987 | Engelmann et al. |
| 4,678,986 | A | 7/1987 | Barthelemy |
| 4,679,560 | A | 7/1987 | Galbraith |
| 4,716,353 | A | 12/1987 | Engelmann |
| 4,717,889 | A | 1/1988 | Engelmann |
| 4,741,339 | A | 5/1988 | Harrison et al. |
| 4,808,924 | A | 2/1989 | Cecco et al. |
| 4,837,497 | A | 6/1989 | Leibovich |
| 4,924,171 | A | 5/1990 | Baba et al. |
| 4,925,443 | A | 5/1990 | Heilman et al. |
| 4,944,299 | A | 7/1990 | Silvian |
| 5,000,178 | A | 3/1991 | Griffith |
| 5,004,489 | A | 4/1991 | Rotman |
| 5,109,843 | A | 5/1992 | Melvin et al. |
| 5,214,392 | A | 5/1993 | Kobayashi et al. |
| 5,312,439 | A | 5/1994 | Loeb |
| 5,314,453 | A | 5/1994 | Jeutter |
| 5,324,316 | A | 6/1994 | Schulman et al. |
| 5,350,411 | A | 9/1994 | Ryan et al. |
| 5,350,413 | A | 9/1994 | Miller |
| 5,355,296 | A | 10/1994 | Kuo et al. |
| 5,358,514 | A | 10/1994 | Schulman et al. |
| 5,383,912 | A | 1/1995 | Cox et al. |
| 5,411,536 | A | 5/1995 | Armstrong |
| 5,411,537 | A | 5/1995 | Munshi et al. |
| 5,480,415 | A | 1/1996 | Cox et al. |
| 5,506,503 | A | 4/1996 | Cecco et al. |
| 5,527,348 | A | 6/1996 | Winkler et al. |
| 5,545,191 | A | 8/1996 | Mann et al. |
| 5,556,421 | A | 9/1996 | Prutchi et al. |
| 5,569,156 | A * | 10/1996 | Mussivand ............ 600/16 |
| 5,613,935 | A | 3/1997 | Jarvik |
| 5,621,369 | A | 4/1997 | Gardner et al. |
| 5,630,836 | A | 5/1997 | Prem et al. |
| 5,690,693 | A | 11/1997 | Wang et al. |
| 5,702,431 | A | 12/1997 | Wang et al. |
| 5,713,939 | A | 2/1998 | Nedungadi et al. |
| 5,722,998 | A | 3/1998 | Prutchi et al. |
| 5,730,125 | A | 3/1998 | Prutchi et al. |
| 5,733,313 | A * | 3/1998 | Barreras et al. ............ 607/33 |
| 5,735,887 | A | 4/1998 | Barreras, Sr. et al. |
| 5,740,257 | A | 4/1998 | Marcus |
| 5,741,316 | A | 4/1998 | Chen et al. |
| 5,749,909 | A | 5/1998 | Schroeppel et al. |
| 5,755,748 | A | 5/1998 | Borza et al. |
| 5,861,019 | A | 1/1999 | Sun |
| 5,948,006 | A | 9/1999 | Mann |
| 5,951,459 | A | 9/1999 | Blackwell |
| 5,959,522 | A | 9/1999 | Andrews |
| 5,963,132 | A | 10/1999 | Yoakum |
| 5,978,713 | A | 11/1999 | Prutchi et al. |
| 5,991,665 | A | 11/1999 | Wang et al. |
| 5,995,874 | A | 11/1999 | Borza et al. |
| 6,047,214 | A | 4/2000 | Mueller et al. |
| 6,048,601 | A | 4/2000 | Yahagi et al. |
| 6,058,330 | A | 5/2000 | Borza et al. |
| 6,067,474 | A | 5/2000 | Schulman et al. |
| 6,141,592 | A | 10/2000 | Pauly |
| 6,144,841 | A | 11/2000 | Feeney |
| 6,149,683 | A | 11/2000 | Lancisi et al. |
| 6,212,430 | B1 | 4/2001 | Kung |
| 6,243,608 | B1 | 6/2001 | Pauly et al. |
| 6,275,737 | B1 | 8/2001 | Mann |
| 6,278,258 | B1 | 8/2001 | Echarri et al. |
| 6,321,118 | B1 | 11/2001 | Hahn |
| 6,324,430 | B1 | 11/2001 | Zarinetchi et al. |
| 6,324,431 | B1 | 11/2001 | Zarinetchi et al. |
| 6,327,504 | B1 | 12/2001 | Dolgin et al. |
| 6,349,234 | B2 | 2/2002 | Pauly et al. |
| 6,366,817 | B1 | 4/2002 | Kung |
| 6,389,318 | B1 | 5/2002 | Zarinetchi et al. |
| 6,395,027 | B1 | 5/2002 | Snyder |
| 6,400,991 | B1 | 6/2002 | Kung |
| 6,415,186 | B1 | 7/2002 | Chim et al. |
| 6,430,444 | B1 | 8/2002 | Borza et al. |
| 6,442,434 | B1 | 8/2002 | Zarinetchi et al. |
| 6,443,891 | B1 | 9/2002 | Grevious |
| 6,445,956 | B1 | 9/2002 | Laird et al. |
| 6,478,820 | B1 | 11/2002 | Weiss |
| 6,496,733 | B2 | 12/2002 | Zarinetchi et al. |
| 6,507,759 | B1 | 1/2003 | Prutchi et al. |
| 6,542,777 | B1 | 4/2003 | Griffith et al. |
| 6,553,263 | B1 * | 4/2003 | Meadows et al. ............ 607/61 |
| 6,591,139 | B2 | 7/2003 | Loftin et al. |
| 6,631,296 | B1 | 10/2003 | Parramon et al. |
| 6,745,077 | B1 | 6/2004 | Griffith et al. |
| 6,772,011 | B2 | 8/2004 | Dolgin |
| 6,959,213 | B2 | 10/2005 | Prutchi et al. |
| 6,959,217 | B2 | 10/2005 | DelMain et al. |
| 6,968,234 | B2 | 11/2005 | Stokes |
| 7,015,769 | B2 | 3/2006 | Schulman et al. |
| 7,027,871 | B2 | 4/2006 | Burnes et al. |
| 7,062,331 | B2 | 6/2006 | Zarinetchi et al. |
| 7,076,304 | B2 | 7/2006 | Thompson |
| 7,079,901 | B1 | 7/2006 | Loftin et al. |
| 7,092,762 | B1 | 8/2006 | Loftin et al. |
| 7,151,914 | B2 | 12/2006 | Brewer |
| 7,155,291 | B2 | 12/2006 | Zarinetchi et al. |
| 7,177,690 | B2 | 2/2007 | Woods et al. |
| 7,184,836 | B1 | 2/2007 | Meadows et al. |
| 7,191,007 | B2 | 3/2007 | Desai et al. |
| 7,225,032 | B2 | 5/2007 | Schmeling et al. |
| 7,237,712 | B2 | 7/2007 | DeRocco et al. |
| 7,248,929 | B2 | 7/2007 | Meadows et al. |
| 7,286,880 | B2 | 10/2007 | Olson et al. |
| 7,286,881 | B2 | 10/2007 | Schommer et al. |
| 7,295,878 | B1 | 11/2007 | Meadows et al. |
| 7,308,316 | B2 | 12/2007 | Schommer |
| 7,418,297 | B2 | 8/2008 | Bornhoft et al. |
| 7,437,644 | B2 | 10/2008 | Ginggen et al. |
| 7,471,986 | B2 | 12/2008 | Hatlestad |
| 7,482,783 | B2 | 1/2009 | Schommer |
| 7,512,443 | B2 | 3/2009 | Phillips et al. |
| 7,515,012 | B2 | 4/2009 | Schulman et al. |
| 7,515,967 | B2 | 4/2009 | Phillips et al. |
| 7,532,932 | B2 | 5/2009 | Denker et al. |
| 7,599,743 | B2 | 10/2009 | Hassler, Jr. et al. |
| 7,599,744 | B2 | 10/2009 | Giordano et al. |
| 7,632,235 | B1 | 12/2009 | Karicherla |
| 7,658,196 | B2 | 2/2010 | Ferreri et al. |
| 7,689,176 | B2 | 3/2010 | Crivelli |
| 7,711,435 | B2 | 5/2010 | Schommer |
| 7,738,965 | B2 | 6/2010 | Phillips et al. |
| 7,751,899 | B1 | 7/2010 | Karunasiri |
| 7,751,902 | B1 | 7/2010 | Karunasiri |
| 7,775,444 | B2 | 8/2010 | DeRocco et al. |
| 7,813,801 | B2 | 10/2010 | Youker et al. |
| 7,818,068 | B2 | 10/2010 | Meadows et al. |
| 7,822,480 | B2 | 10/2010 | Park et al. |
| 7,848,814 | B2 | 12/2010 | Torgerson et al. |
| 7,856,986 | B2 | 12/2010 | Darley |
| 2002/0016568 | A1 | 2/2002 | Lebel et al. |
| 2003/0088295 | A1 | 5/2003 | Cox et al. |
| 2003/0163020 | A1 | 8/2003 | Frazier |
| 2003/0171792 | A1 | 9/2003 | Zarinetchi et al. |
| 2004/0039423 | A1 | 2/2004 | Dolgin |
| 2005/0075693 | A1 | 4/2005 | Toy et al. |
| 2005/0075696 | A1 | 4/2005 | Forsberg et al. |
| 2005/0107847 | A1 | 5/2005 | Gruber et al. |
| 2005/0113887 | A1 | 5/2005 | Bauhahn et al. |
| 2005/0288739 | A1 | 12/2005 | Hassler et al. |
| 2005/0288740 | A1 | 12/2005 | Hassler et al. |

(56) References Cited

U.S. PATENT DOCUMENTS

| | | | |
|---|---|---|---|
| 2005/0288743 | A1 | 12/2005 | Ahn et al. |
| 2006/0020300 | A1 | 1/2006 | Nghiem et al. |
| 2006/0020305 | A1 | 1/2006 | Desai et al. |
| 2006/0107148 | A1 | 5/2006 | Ginggen et al. |
| 2006/0197494 | A1 | 9/2006 | Schommer |
| 2006/0247737 | A1 | 11/2006 | Olson et al. |
| 2007/0049983 | A1 | 3/2007 | Freeberg |
| 2007/0106274 | A1 | 5/2007 | Ayre et al. |
| 2007/0142696 | A1 | 6/2007 | Crosby et al. |
| 2007/0255349 | A1 | 11/2007 | Torgerson et al. |
| 2007/0270921 | A1 | 11/2007 | Strother et al. |
| 2008/0027500 | A1 | 1/2008 | Chen |
| 2008/0027513 | A1 | 1/2008 | Carbunaru |
| 2008/0065290 | A1 | 3/2008 | Breed |
| 2008/0129517 | A1* | 6/2008 | Crosby et al. ............. 340/573.1 |
| 2008/0167531 | A1 | 7/2008 | McDermott |
| 2008/0312852 | A1 | 12/2008 | Maack |
| 2009/0069869 | A1 | 3/2009 | Stouffer et al. |
| 2009/0157148 | A1 | 6/2009 | Phillips et al. |
| 2009/0273349 | A1 | 11/2009 | Rondoni et al. |
| 2009/0276016 | A1 | 11/2009 | Phillips et al. |
| 2010/0063347 | A1 | 3/2010 | Yomtov |
| 2010/0076524 | A1 | 3/2010 | Forsberg et al. |
| 2010/0080025 | A1 | 4/2010 | Terlizzi |
| 2010/0222848 | A1 | 9/2010 | Forsell |
| 2010/0305662 | A1 | 12/2010 | Ozawa et al. |
| 2010/0312188 | A1 | 12/2010 | Robertson |
| 2011/0009924 | A1 | 1/2011 | Meskens |
| 2011/0101790 | A1 | 5/2011 | Budgett |
| 2011/0160516 | A1* | 6/2011 | Dague et al. ................... 600/16 |
| 2012/0157753 | A1 | 6/2012 | D'Ambrosio |
| 2012/0157754 | A1 | 6/2012 | D'Ambrosio |
| 2012/0157755 | A1 | 6/2012 | D'Ambrosio |
| 2012/0265003 | A1 | 10/2012 | D'Ambrosio |
| 2013/0158631 | A1 | 6/2013 | Shea et al. |

FOREIGN PATENT DOCUMENTS

| | | |
|---|---|---|
| JP | 07-046164 A | 2/1995 |
| JP | 2010-284065 A | 12/2010 |
| WO | 97/29802 A2 | 8/1997 |
| WO | 97/47065 A1 | 12/1997 |
| WO | 99/44684 A1 | 9/1999 |
| WO | 2006096685 A1 | 9/2006 |
| WO | 2008/106717 A1 | 9/2008 |
| WO | 2011008163 A1 | 1/2011 |

OTHER PUBLICATIONS

[No Author Listed] Low-power SoC (system-on-chip) with MCU, memory sub-1 ghz RF transceiver, and USB controller. TIRF Common Spec (CC1110Fx/CC1111Fx), Texas Instruments, Jul. 20, 2010, 247 pages.

[No Author Listed]Battery Spec NCR 18650. NNP Series. Panasonic. Feb. 2010, 1 page.

Abe et al., Development of transcutaneous energy transmission system for totally implantable artificial heart. Artificial Heart 2/Proceedings of the 2nd International Symposium on Artificial Heart and Assist Device. Akutsu, T. ed, Springer-Verlag, Tokyo, pp. 257-261, 1988.

Ahn et al., In Vivo Performance Evaluation of a Transcutaneous Energy and Information Transmission System for the Total Artificial Heart, ASAIO Journal 1993, M208-M212.

Barsukov, Theory and Implementation of Impedance Track™ Battery Fuel-Gauging Algorithm in bq20z8x Product Family, Texas Instruments, SLUA364, Nov. 2005. 8 pages.

Bearnson et al., Electronics Development for the Utah Electrohydrolic Total Artificial Heart. Sixth Annual IEEE Symposium on Computer-Based Medical Systems, 247-252 (1993).

Callewaert et al., A Programmable Implantable Stimulator with Percutaneous Optical Control. Ninth Annual Conference of the Engineering in Medicine and Biology Society IEEE, 1370-1371 (1987).

Davies et al., Adaptation of Tissue to a Chronic Heat Load, ASAIO Journal. 40(3), M514-7 (1994).

Donaldson, Nde N, Use of feedback with voltage regulators for implants powered by coupled coils. Med Biol Eng Comput. May 1985;23(3):291, XP002066875, ISSN: 0140-0118.

Fraim et al. Performance of a tuned ferrite core transcutaneous transformer. IEEE Trans Bio-med Eng. Sep. 1971; BME-18(5):352-9.

Galbraith et al, A Wide-Band Efficient Inductive Transdermal Power and Data Link with Coupling Insensitive Gain. IEEE Transactions on Biomedical Engineering, BME 34(4):265-275 (1987).

Geselowitz et al., The effects of metals on a transcutaneous energy transmission system. IEEE Transactions on Biomedical Engineering. vol. 39(9), pp. 928-934, Sep. 1992.

International Search Report and Written Opinion for Application No. PCT/US2011/065471, mailed Aug. 29, 2012. (10 pages).

Masuzawa, T., et al., Set-up, Improvement, and Evaluation of an Electrohydraulic Total Artificial Heart with a Separately Placed Energy Converter. (1996) ASAIO Journal, vol. 42; M328-M332.

Matsuki et al. Energy Transferring System Reducing Temperature Rise for Implantable Power Consuming Devices. Proceedings of the 18th Annual Conference of the IEEE Engineering in Medicine and Biology Society, Amsterdam Oct. 31-Nov. 3, 1996, vol. 1, pp. 185-186.

Matsuki et al., Signal Transmission for Implantable Medical Devices using Figure-of-eight Coils, IEEE Transactions on Magnetics, vol. 32 No. 5, pp. 5121-5123, Sep. 1996.

Melvin, D.B., et al., Electric Power Induction Through an Isolated Intestinal Pouch. (1991) Trans. Am. Soc. Intern. Organs, vol. XXXVII;M203-M204.

Miller et al. Development of an Autotuned Transcutaneous Energy Transfer System. ASAIO Journal. 1993;39:M706-M710.

Mitamura et al., Development of an Implantable Motor-Driven Assist Pump System. IEEE Transactions on Biomedical Engineering. vol. 37(2), pp. 146-156, 1990.

Mitamura et al. A Transcutaneous Optical Information Transmission System for Implantable Motor-drive Artificial Hearts. ASAIO Transactions. 1990;36:M278-M280.

Mohammed et al. A miniature DC-DC converter for energy producing implantable devices. IEEE Ninth Annual Conference of the Engineering in Medicine and Biology Society, 1147-1148, 1987.

Mohammed, Design of radio frequency powered coils for implantable stimulators. IEEE Ninth Annual Conference of the Engineering in Medicine and Biology Society, 1378-1379, 1987.

Mussivand et al. Remote energy transmission for powering artificial hearts and assist devices. Artificial Heart 6/6th International Symposium on Artificial Heart and Assist Devices. Akutsu et al., eds., Springer-Verlag, Tokyo, pp. 344-347, 1998.

Mussivand et al. Transcutaneous energy transfer system performance evaluation. Artificial Organs. May 1993;17 (11):940-947.

Myers et al. A transcutaneous power transformer. Transactions of the American Society for Artificial Internal Organs, vol. 14, pp. 210-214, 1968.

Phillips, R.P., A High Capacity Transcutaneous Energy Transmission System. ASAIO Journal, vol. 41: M259-M262 (1995).

Rintoul et al, Continuing Development of the Cleveland Clinic-Nimbus Total Artificial Heart. ASAIO Journal, 39: M168-171 (1993).

Rosenberg et al., Progress Towards a Totally Implantable Artificial Heart. Cardiovascular Science & Technology: Basic & Applied, I. Precised Proceedings, pp. 214-216 (1989-1990).

Sherman et al., Energy Transmission Across Intact Skin for Powering Artificial Internal Organs. Trans. Am. Soc. Artificial Intern Organs, vol. XXVII, 1981, pp. 137-141.

Sherman et al., Transcutaneous energy transmission (TET) system for energy intensive prosthetic devices. Progress in Artificial Organs. 1985;400-404.

Sutton, A miniaturized device for electrical energy transmission through intact skin-concepts and sesults of initial tests. Third Meeting of the International Society for Artificial Organs. vol. 5, abstracts, Jul. 1981, pp. 437-440.

Weiss et al. A telemetry system for the implanted total artificial heart and ventricular assist device. IEEE Ninth Annual Conference of the Engineering in medicine and Biology Society, pp. 186-187, 1987.

Weiss et al., Permanent Circulatory Support at the Pennsylvania State University. IEEE Transaction on Biomedical Engineering 37(2):138-145 (Feb. 1990).

\* cited by examiner

TRANSCUTANEOUS ENERGY TRANSFER SYSTEM WITH VIBRATION INDUCING WARNING CIRCUITRY

RELATED APPLICATIONS

This application claims priority to U.S. Provisional Application Ser. No. 61/425,164, filed on Dec. 20, 2010, and entitled "Transcutaneous Energy Transfer System with Vibration Inducing Warning Circuitry."

FIELD

The invention relates to transcutaneous energy transfer (TET) systems and more particularly to an improved alarm device for use in a TET system that generates an internal vibratory alarm.

BACKGROUND

Many medical devices adapted for implantation also have high power requirements and must be frequently connected to external power sources. Inductively coupled transcutaneous energy transfer (TET) systems are increasingly popular for use in connection with these high-power implantable devices. A TET system may be employed to supplement, replace, or charge an implanted power source, such as a rechargeable battery. Unlike other types of power transfer systems, TET systems have an advantage of being able to provide power to the implanted electrical and/or mechanical device, or recharge the internal power source, without puncturing the skin. Thus, possibilities of infection are reduced and comfort and convenience are increased.

TET devices include an external primary coil and an implanted secondary coil, separated by intervening layers of tissue. The primary coil is designed to induce alternating current in the subcutaneous secondary coil, typically for transformation to direct current to power an implanted device. TET devices therefore also typically include an oscillator and other electrical circuits for periodically providing appropriate alternating current to the primary coil. These circuits typically receive their power from an external power source.

TET systems commonly include an implanted controller that can be used to monitor and control any implanted devices. If a fault is detected in the implanted device or another component of the TET system, there is a need for the controller to notify the patient or a nearby healthcare professional.

SUMMARY

To overcome the above and other drawbacks of conventional systems, the present invention provides an alarm device for use in a transcutaneous energy transfer (TET) system.

One aspect of the invention provides an alarm device for use in a transcutaneous energy transfer system including a processor configured to monitor at least one function of an implanted cardiac assist device and to generate an internal vibratory alarm.

In one embodiment, the processor can be configured to monitor the energy level of a battery connected to the implanted cardiac assist device.

In another embodiment, the alarm device can be further configured to generate an internal vibratory alarm when the energy level of the battery reaches a predetermined threshold level.

In still another embodiment, the alarm device can be located in a single biocompatible housing that may include a rechargeable battery pack and control modules for controlling a cardiac assist device.

In another embodiment, the alarm device can be implanted in the body.

A second aspect of the invention provides a transcutaneous energy transfer system including one or more secondary coils, one or more primary coils, a rechargeable battery pack, a control module, an alarm module, and a processor. The one or more secondary coils are adapted for disposition within a patient and to receive energy from the one or more primary coils. The one or more primary coils are adapted for disposition outside the patient. The control module is adapted to control a cardiac assist device and the alarm module is adapted to produce a vibratory alarm. The processor is configured to monitor the battery pack, secondary coils, and cardiac assist device and alert the patient to any abnormal operating conditions with a vibratory alarm.

In some embodiments, the rechargeable battery pack, control module, alarm module, and processor can be contained in a single biocompatible housing adapted for disposition within a patient.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the devices disclosed herein. One or more examples of these embodiments are illustrated in the accompanying drawings. Those skilled in the art will understand that the devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A transcutaneous energy transfer (TET) system works by inductively coupling a primary coil to a secondary coil. The primary coil, configured for disposition outside a patient, is connected to a power source and creates a time-varying magnetic field. When properly aligned with a secondary coil, the time-varying magnetic field from the primary coil induces an alternating electric current in the secondary coil. The secondary coil is configured for implantation inside a patient and can be connected to a controller that harnesses the electric current and uses it to, for example, charge a battery pack or power an implantable device like a ventricular assist device (VAD), or other cardiac assist device. By utilizing induction to transfer energy, TET systems avoid having to maintain an open passage through a patient's skin to power an implantable device.

TET systems include an implanted rechargeable battery pack that allows a patient to spend some amount of time disconnected from the external primary coil and power source. A controller connected to the rechargeable battery pack and implanted cardiac assist device is configured to monitor the devices for faults or low-charge conditions.

The present invention provides an internal alarm device for signaling a patient when a fault or low-charge condition occurs and the patient is not in close proximity to an external monitor device. The alarm device monitors the implanted device and battery pack and generates a vibratory alarm in the event of a fault or low-charge condition.

Figure 1:
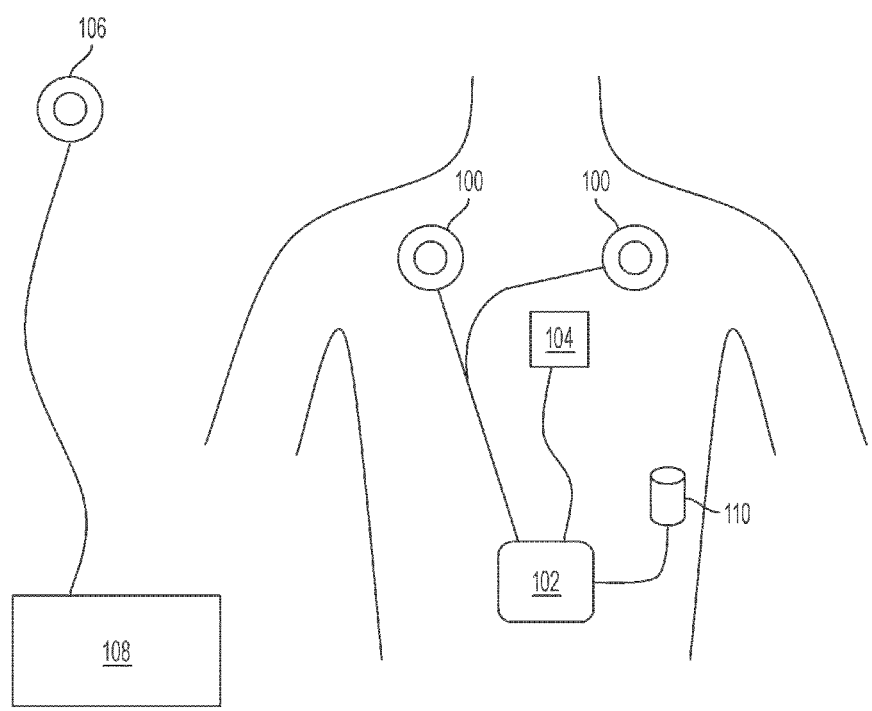
FIG. 1 is a diagram of an exemplary TET system of the present invention.
Figure 5:
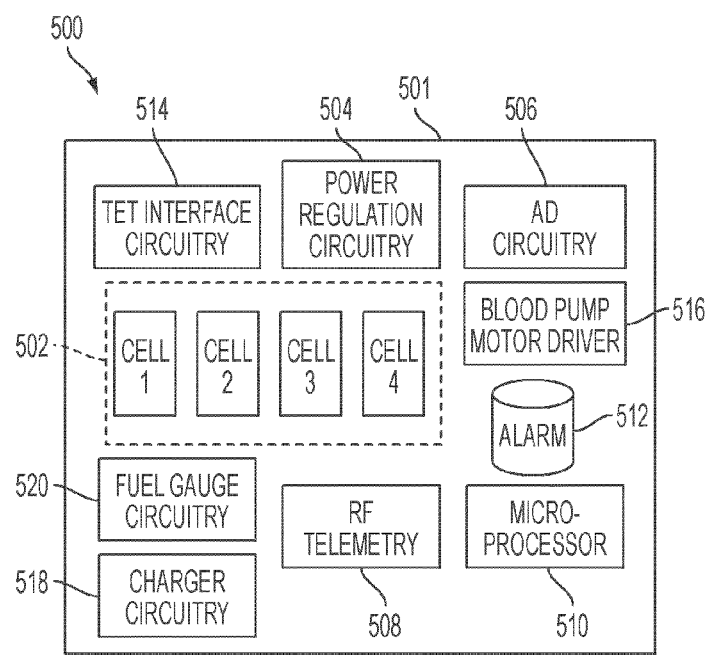
FIG. 5 is a diagram of an exemplary implantable controller containing power and control circuitry, as well as a rechargeable battery pack and alarm device.

FIG. 1 shows a diagram of an exemplary TET system of the present invention. An implantable device comprises one or more secondary coils 100 adapted for disposition in a patient. The secondary coils are connected to a controller 102 that is adapted to receive electric current from a single or plurality of secondary coils for use or storage. The controller can then direct the electric current to, for example, charge a battery (which can be integrated with controller 102) or power a ventricular assist device 104 or other implantable device. In FIG. 1, the controller 102 is also connected to vibratory alarm device 110 that generates the vibratory signal in the event of a fault or low-charge condition. While vibratory alarm device 110 is shown separate from controller 102, in other embodiments it can be incorporated into controller 102, as shown in FIG. 5. In either case, the vibratory alarm device 110 or integrated controller 102 can be positioned in the body of a patient such that the patient can distinguish between vibrations of the alarm device and other externally induced vibrations (e.g., vibrations from riding in a car).

FIG. 1 also shows an exemplary embodiment of primary coil 106 that is adapted to remain outside the body and transfer energy inductively to the secondary coils. Primary coil 106 is connected to an external power source, which can include, for example, conditioning and control circuitry. Optionally, more than one primary coil 106 can be used simultaneously with the multiple secondary coils 100 to reduce the time required to charge an implanted battery.

In use, primary coil(s) 106 are placed over the area of secondary coils 100 such that they are substantially in axial alignment. Power source 108, which can include conditioning circuitry to produce a desired output voltage and current profile, is then activated to produce a time-varying magnetic field in the primary coil(s) 106. The time-varying magnetic field induces an electric current to flow in the secondary coils 100 and the current is subsequently distributed to controller 102 and any attached ventricular assist devices 104 or charge storage devices.

Figure 2:
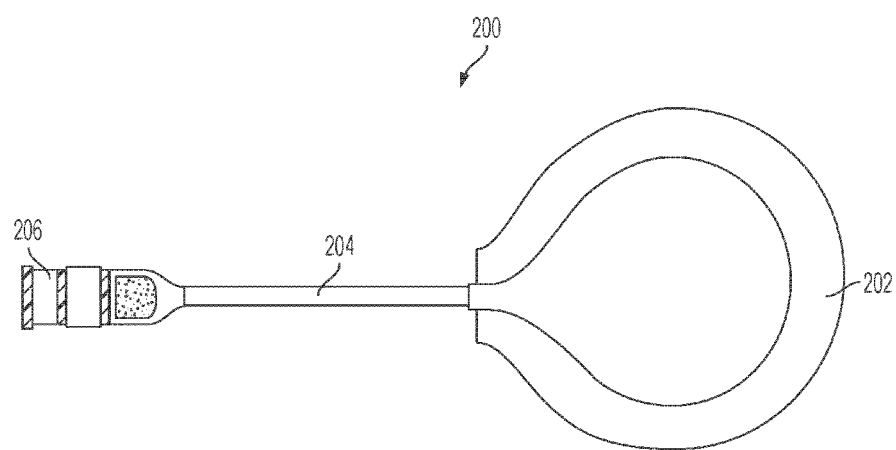
FIG. 2 is an illustration of an exemplary implantable secondary coil.

FIG. 2 illustrates an exemplary secondary coil 200 adapted for disposition in a patient. Secondary coil 200 features a coil portion 202 consisting of several turns of conductive wire, a connecting portion 204, and an optional interface portion 206. Coil portion 202 can vary in size and turns of wire depending on numerous factors such as the intended implantation site. In an exemplary embodiment, coil portion 202 comprises 12 turns of Litz wire in a two-inch diameter coil. In addition to the wire, the coil 202 can contain a ferrous core and electronic circuitry which rectifies the AC current and communicates with the external coil and driver to provide a regulated DC output voltage. An exemplary secondary coil is described in U.S. Patent Pub. No. 2003/0171792, which is incorporated herein by reference.

The coil portion 202 is electrically coupled to the connecting portion 204, which can be formed from a segment of the same wire used to form the coil portion. The length of connecting portion 204 can also vary based on, for example, the distance from the implantation site of a secondary coil to that of a controller.

Connecting portion 204 is also electrically coupled to optional interface portion 206. Interface portion 206 is used to connect the secondary coil 200 to a controller 102. The interface portion can include any electrical connector known in the art to facilitate modular connection to a controller 102, or can consist of a terminal end of the connecting portion 204 that is capable of being electrically connected to a controller.

Figure 3:
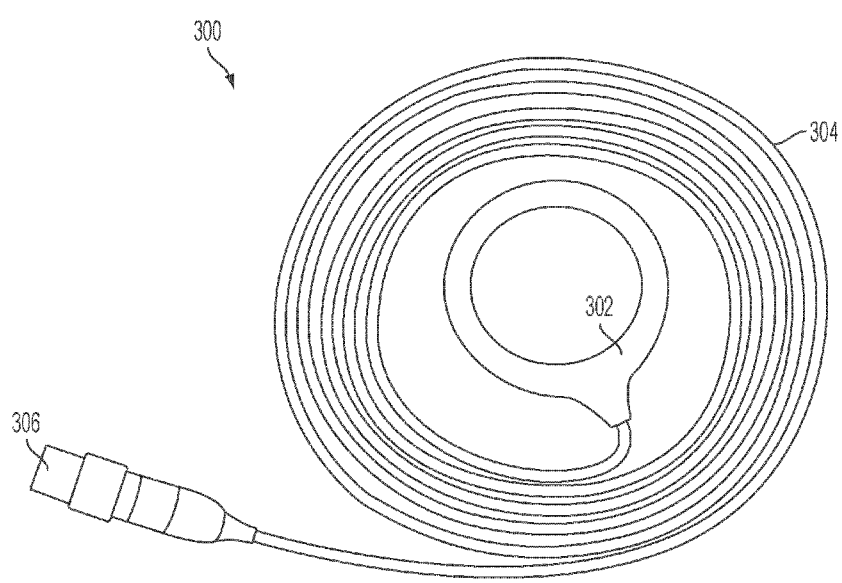
FIG. 3 is an illustration of an exemplary primary coil.

FIG. 3 shows an exemplary primary coil 300 configured to transmit transcutaneous energy to a secondary coil like that illustrated in FIG. 2. Similar to secondary coil 200 in FIG. 2, primary coil 300 can include a coil portion 302, a connecting portion 304, and an interface portion 306. Primary coil 300 is adapted for disposition outside the patient, however, and induces electric current in secondary coil 200 by emitting a time-varying magnetic field from coil portion 302.

Coil portion 302 can vary in size and turns of wire depending on several factors including, for example, the size of any secondary coils it will be used with. Coil portion 302 is electrically coupled to connecting portion 304. Connecting portion 304 can be formed from a portion of the wire used to form coil portion 302. Connecting portion 304 can vary in length depending on any of several factors including, for example, how far a patient is from a power source. Connecting portion 304 is in turn electrically coupled to interface portion 306, which is adapted to connect to a power source (or associated conditioning or control circuitry) like power source 108 of FIG. 1. Interface portion 306 can include any electrical connector known in the art to facilitate modular connections to external power source 108, or can consist of a terminal end of connecting portion 304 that is adapted to be electrically connected to power source 108.

Figure 4:
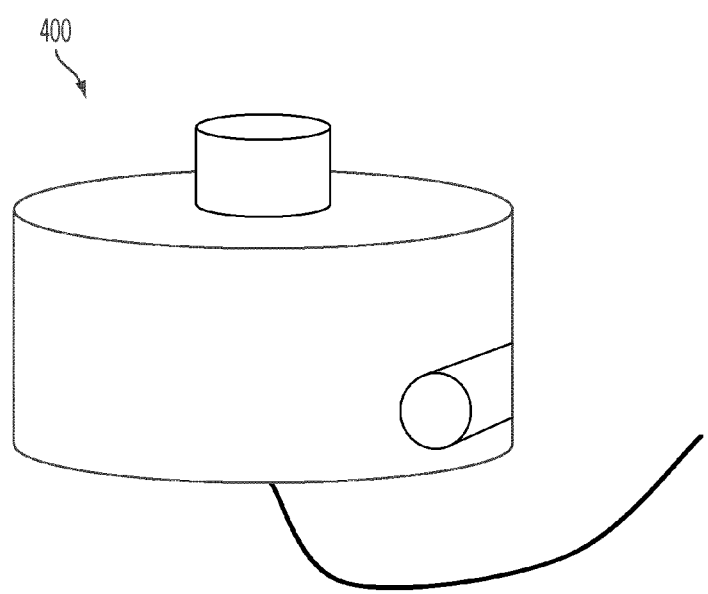
FIG. 4 is a front perspective view of an exemplary ventricular assist device powered by a TET system.

Primary coil 300 is used to transfer power transcutaneously in order to ultimately support an implantable device like the ventricular assist device (VAD) 400 depicted in FIG. 4. The ventricular assist device 400 aids the heart in circulating blood through the body. While a ventricular assist device is an exemplary embodiment of an implantable device that can benefit from TET systems, it is by no means the only implantable device that can be powered in this way. Other cardiac assist devices, as well as many other types of powered implantable devices, can be used with the system of the present invention.

FIG. 1 shows the secondary coils 100 connected to the ventricular assist device 104 via a controller like that illustrated in FIG. 5. FIG. 5 depicts an integrated controller and battery pack 500 that is adapted for disposition in a patient. Controller and battery pack 500 has a single biocompatible housing 501 that encapsulates the rechargeable battery cells 502 and all of the control circuitry. Controller 500 can also be implemented without the use of a single biocompatible housing 501. In such cases, each individual component can have a biocompatible housing and the components can be connected using wires or other known methods of electrical communication.

The controller and battery pack 500 includes a control module comprising power monitoring and regulation circuitry 514, 504, and 518, A/D circuitry 508, blood pump motor driver 516, and RF telemetry module 508. The controller and battery pack 500 also includes alarm device 512 and microprocessor 510.

Electric current received from the secondary coil(s) 100 is processed through the TET interface circuitry 514 and conditioned for use with the battery cells 502 through the charger circuitry 518 or to power the internal electronics and ventricular assist device 104 by power regulation circuitry 504. Power regulation circuitry 504 can contain any of several circuit designs known in the art that are effective to convert the voltage and current received from the TET interface circuitry 514 into a desired output voltage and current that can be used to power the internal electronic circuitry 506, 508, 510, 512 and the ventricular assist device 104 via the blood pump motor driver 516.

Controller 500 can also include VAD circuitry 506 and 516 that is configured to control the ventricular assist device 104. The VAD circuitry can include monitoring features so that any failures in the ventricular assist device 104 are detected in the controller 500. The controller 500 can further include a central processor 510 that coordinates functions executed by the charger circuitry 518, power regulation circuitry 504, blood pump motor driver circuitry 516, and A/D circuitry 506.

The processor 510 can also monitor the function of secondary coils 100 along with the ventricular assist device 104. If a fault is detected in either component, processor 510 can signal a user in several ways. If available, RF telemetry module 508 can be utilized to communicate fault information via an external display or control console. The display or control console could take the form of a common desktop computer, mobile phone, PDA, bed-side control console, or any other type of computing or signaling device known in the art.

With the controller of the present invention, fault information can also be communicated in the form of a vibratory alarm generated by alarm module 512. The vibratory alarm can serve as a primary warning in cases where the patient is mobile and located away from any external displays or control consoles, and can serve as a redundant secondary warning system when RF telemetry module 508 is able to communicate with an external display or control console.

Controller 500 can also feature fuel gauge circuitry 520 that is configured to measure both the current charge remaining in battery cells 502 and the power consumption rate of VAD 104. To determine remaining charge, fuel gauge circuitry 520 can record metrics such as battery impedance, open-circuit voltage, temperature, discharge rate, and cell aging. The resulting measurement can be more accurate than prior art systems that gauge charge based on voltage alone. An exemplary system for accurately determining battery charge is the bq20z95 platform by Texas Instruments, Inc. featuring the Impedance Track™ gauging technology. More information on this system can be found at http://focus.ti.com/lit/an/slua364/slua364.pdf and http://focus.ti.com/lit/ds/slus757b/slus757b.pdf. These publications are hereby incorporated in their entirety.

After determining an accurate level of charge remaining in the battery cells 502 and the power consumption rate of the VAD 104, fuel gauge circuitry 520 or microprocessor 510 can compute the remaining time, based on the current level of consumption, until the battery reaches a predetermined threshold level.

The predetermined threshold level can be set above the level of battery exhaustion to provide some reserve time and allow a patient to get to an external power source. In addition, multiple threshold levels may be set to provide a patient with multiple warnings as the battery exhausts itself.

The microprocessor 510 can use RF telemetry module 508 or alarm module 512 to communicate the remaining time to a user. For example, the RF telemetry module 508 can be used to communicate the remaining time to a user via an external display. The external display may be any display known in the art, including displays integrated in control consoles or diagnostic equipment, PDAs, laptop or desktop computers, etc.

If a patient is away from any external display and external alarm (visual and/or audible), the microprocessor 510 can utilize alarm device 512 to generate a vibratory alarm warning of the fault or low-charge condition of the battery. One of skill in the art will appreciate that many different combinations of these warnings may be implemented. For example, the alarm device 512 can be used to generate a vibratory alarm even when the patient is within range of an external display. In other embodiments, the RF telemetry module 508 may be used to communicate with a vibratory alarm device located outside the controller 500, and possibly even outside the patient, e.g. located on a nearby healthcare professional.

The vibratory signal generated by the vibratory alarm device 512 can be a series of on-off or timed pulses that can be set by a user or healthcare professional. This can include, for example, a variable intensity vibratory buzzer that can be located near the cochlea bone or other structure in order to generate an audible alarm for the patient. The system can also be used to stimulate a muscle to induce a twitch or other body movement.

Different patterns of vibration can be used to convey different levels of urgency to the patient. For example, if the threshold level was set to 30 minutes, when the capacity of the battery cells 502 reaches 30 minutes the alarm module 512 may create a vibratory signal for 3 seconds every 30 seconds until the external power source is applied. Additionally, a critically low threshold level may be set to 15 minutes and, when the capacity of the battery cells 502 reaches that level, the alarm module 512 may create a vibratory signal for 3 seconds every 10 seconds until the external TET is applied. The alarm thresholds and vibrator patterns are configurable in software depending on patient, healthcare professional, or manufacturer requirements.

Figure 6:
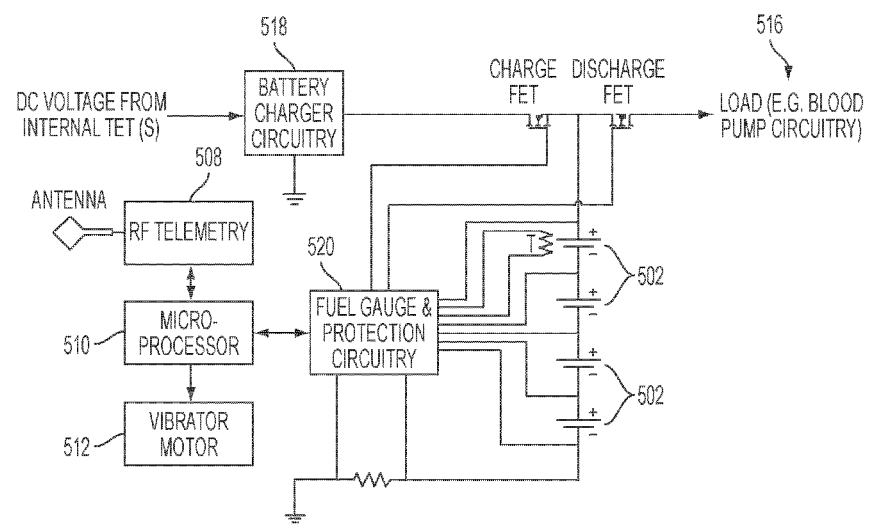
FIG. 6 is an exemplary circuit diagram of the controller illustrated in FIG. 5.

FIG. 6 illustrates an exemplary circuit diagram for the TET system of the present invention. The diagram illustrates the electrical connections between the VAD circuitry (including blood pump motor driver 516), battery cells 502, fuel gauge circuitry 520, charger circuitry 518, microprocessor 510, RF telemetry module 508, and vibratory alarm device 512. One of skill in the art will appreciate that this is an exemplary circuit diagram only, and there are several other configurations that would also be effective to create the TET system of the present invention.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A transcutaneous energy transfer system, comprising:
   an implantable cardiac assist device
   one or more secondary coils adapted for implantation within a patient in conjunction with the cardiac assist device, the one or more secondary coils further configured to receive energy from one or more primary coils disposed outside the patient by inductive coupling;
   a rechargeable battery pack to store energy received by the secondary coils;
   a control module for controlling the cardiac assist device;
   an alarm module for producing a plurality of different patterns of vibrations; and a processor configured to monitor the battery pack, secondary coils, and cardiac assist device and alert the patient to any abnormal operating conditions with a vibratory alarm, the processor further configured to direct the alarm module to generate different vibration patterns based on different levels of urgency to the patient.

2. The system of claim 1, further comprising a single biocompatible housing containing the rechargeable battery pack, control module, alarm module, and processor.

3. The system of claim 1 wherein the processor is further configured to direct the alarm module to generate different intensities of vibration.

4. The system of claim 1 wherein the processor is further configured to direct the alarm module to generate different timed pulses.

5. The system of claim 1 wherein the different patterns of vibration provide multiple warnings of different degrees of urgency as a battery in the rechargeable battery back exhausts itself.

* * * * *